United States Patent [19]

Chang et al.

[11] Patent Number: 4,734,124
[45] Date of Patent: Mar. 29, 1988

[54] TETRAZOLINONE HERBICIDES

[75] Inventors: Jun H. Chang, Princeton Junction; John W. Lyga, Basking Ridge, both of N.J.

[73] Assignee: FMC Corporation, Philadelphia, Pa.

[21] Appl. No.: 40,681

[22] Filed: Apr. 16, 1987

Related U.S. Application Data

[63] Continuation-in-part of Ser. No. 3,449, Jan. 15, 1987, abandoned.

[51] Int. Cl.$^4$ .................. A01N 43/84; C07D 413/04
[52] U.S. Cl. ............................................ 71/92; 71/88; 544/105
[58] Field of Search ............................. 544/105; 71/92

[56] References Cited

U.S. PATENT DOCUMENTS 4,619,687  10/1986  Haga et al. ..................... 544/105 X
4,640,707   2/1987  Nagano et al. ..................... 544/105

FOREIGN PATENT DOCUMENTS 0170191  2/1986  European Pat. Off. .

8501939  5/1985  PCT Int'l Appl. .

Primary Examiner—Richard L. Raymond
Attorney, Agent, or Firm—Robert M. Kennedy; H. Robinson Ertelt; Abner Sheffer

[57] ABSTRACT

Herbicidal compounds of the formula

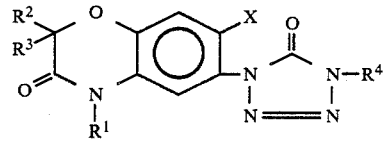

in which
R$^1$ is H, alkyl, alkenyl, alkynyl, haloalkyl, haloalkenyl, haloalkynyl, alkoxyalkyl, alkoxyalkoxyalkyl, alkylsulfonyl, aralkyl, alkylthioalkyl, hydroxy or alkoxy;
R$^2$ and R$^3$ are independently H or alkyl;
X is H, Cl or F;
R$^4$ is alkyl, haloalkyl, alkenyl or alkynyl.

9 Claims, No Drawings

TETRAZOLINONE HERBICIDES

This application is a continuation-in-part, of application Ser. No. 003,449, filed 1-15-87, now abandoned.

TETRAZOLINONE HERBICIDES

This invention relates to tetrazolinones of the following formula I and their use as herbicides:

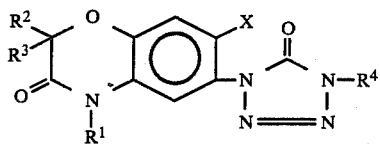
(FORMULA I)

in which $R^1$ is:
H;
alkyl, e.g. methyl, ethyl or propyl;
alkenyl, e.g. allyl or methyallyl;
alkynyl, e.g. propynyl or methypropynyl;
haloalkyl, e.g. 3-chloropropyl;
haloalkenyl, e.g. 2-chloropropenyl;
haloalkynyl, e.g. 3-bromopropynyl;
alkoxyalkyl, e.g. methoxymethyl or ethoxymethyl;
alkoxyalkoxyalkyl e.g. ethoxymethoxymethyl;
alkylsulfonyl, e.g. methylsulfonyl or ethylsulfonyl;
aralkyl, e.g. benzyl;
alkylthioalkyl, e.g. methylthiomethyl;
hydroxy; or alkoxy, e.g. methoxy or ethoxy.
$R^2$ and $R^3$ are, independently
H or alkyl, e.g. methyl, preferably H.
X is H, Cl or F, preferably F.
$R^4$ is alkyl (e.g. methyl or ethyl), haloalkyl (e.g. fluoroalkyl such as $CH_2F$, $CH_2CH_2F$ or $CH_2(CH_2)_2F$), alkenyl (e.g. allyl), alkynyl (e.g. propynyl) or preferably methyl.

In each aspect of the invention it is often preferable that any alkyl, alkenyl, alkynyl or alkylene moiety (such as the hydrocarbon moiety of an alkoxy or haloalkoxy group) have less than 6 carbon atoms, e.g. 1 to 3 carbon atoms.

The compounds of this invention may be prepared by the use of steps generally described in the literature or in the following Examples or by methods analogous or similar thereto and within the skill of the art. In Example 1 below, there is formed a 1-aryl-1,4-dihydro-5H-tetrazol-5-one from an aniline in known manner (such as in the manner taught in published International Application No. WO 85/01939 published May 9, 1985 said application is incorporated herein by reference). The aryltriazinedione is treated to introduce a carboalkoxymethoxy or similar group at the 4-position of the benzene ring and a nitro group at the 5-position to form a compound of the formula

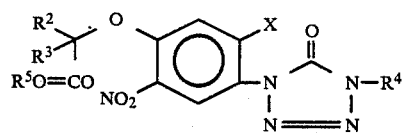

where $OR^5$ is alkoxy or similar group which can be split out in the next step. Then, in known manner (J. Am. Chem. Soc., 81, 94 (1959)) by treatment with iron in an acidified solvent, e.g. at an elevated temperature such as 60°-150° C., reduction of the nitro group to an amino group, followed by ring closure between said 4- and 5-positions is effected, forming a compound of the formula,

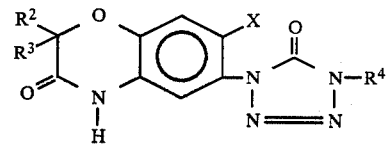

After this an $R^1$ group is introduced, as by reaction with $R^1X^1$ (where $X^1$ is a leaving group such as a halogen) to form the final compound.

To produce compounds in which $R^1$ is hydroxy or alkoxy the reduction and ring closure step may be effected by using a milder reducing agent (such as hydrazine in the presence of rhodium on carbon) to form, during the reaction, an intermediate having a —NHOH group (instead of an —$NH_2$ group) at the 5-position of the benzene ring so that on cyclization there is formed a compound having the formula

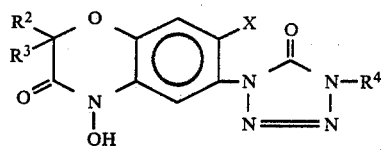

after which that compound is treated with an appropriate alkyl halide (e.g. methyl iodide in the presence of NaH).

To produce compounds in which $R^1$ is haloalkynyl the compound in which $R^1$ is alkynyl may be reacted with the halogen (e.g. iodine or bromine) in the presence of a base (e.g. NaOH or KOH); also a catalyst such as benzyltriethylammonium bromide or chloride or tetrabutylammonium bromide may be present.

In Example 2 below, the appropriate 2H-1,4-benzoxazin-3(4H)-one-6-yl isocyanate, having the desired X and $R^1$ substitutents, is produced. This isocyanate is then converted, in known manner, as by reaction with an azidotrialkylsilane, to the corresponding 2H-1,4-benzoxazin-3(4H-one-6-yl-1,4-dihydro-5H-tetrazol-5-one, after which the $R^4$ group is introduced, as by reaction with $R^4X^1$ (where $X^1$ is a leaving group such as halogen or an alkylsulfonate or arylsulfonate) to form the final compound.

The following Examples are given to illustrate this invention further. In this application all parts are by weight unless otherwise indicated. Also, in the Examples, the mixtures are stirred in conventional fashion and the reaction is carried out in inert atmosphere when appropriate (e.g. in the reaction involving sodium hydride).

EXAMPLE 1

From 4-hydroxy-2-fluoroaniline there is produced (in the manner described in published PCT International Application No. WO 85/01939 published May 9, 1985) 1-(4-hydroxy-2-fluorophenyl)-1,4-dihydro-4-(3-fluoropropyl) -5H-tetrazol-5-one. The latter is the nitrated by treatment with a mixture of $HNO_3$ and $H_2SO_4$ to form 1-(4-hydroxy-2-fluoro-5-nitrophenyl)-1,4-dihydro-4-(3-fluoropropyl)-5H-tetrazol-5-one. The latter is then dissolved in N,N-dimethylformamide ("DMF") and mixed with a dispersion of NaH in DMF, after which a solution of ethyl bromoacetate is added, resulting in a reaction yielding 1-(4-carboethoxy-methoxy-2-fluoro-5-nitrophenyl)-1,4-dihydro-4-(3-fluoropropyl)-5H-tetrazol-5-one. The latter is then dissolved in acetic acid and then added to a hot suspension of iron powder in acetic acid and reacted at elevated temperature (e.g. 80°–90° C.) for about an hour to form 1-(7-fluoro-2H-1,4-benzoxazin-3(4H)-one-6-yl)1,4-dihydro-4-(3-fluoropropyl)-5H-tetrazol-5-one. The latter is then dissolved in DMF and added to a suspension of NaH in DMF and warmed to, e.g 50° C. Then a solution of 1-iodopropane in DMF is added and the mixture allowed to react to form 1-[7-fluoro-4-propyl-2H-1,4-benzoxazin-3(4H)-on-6-yl]-1,4-dihydro-4-(3-fluoropropyl)-5H-tetrazol-5-one.

Instead of the iodopropane one may substitute other reactive halides in the last step, so as to form the corresponding compounds having other $R^1$ substituents, e.g. methyl iodide, ethyl iodide, propargyl bromide, methoxymethyl bromide, methylthiomethyl chloride, benzyl bromide and ethylsulfonyl chloride to form, respectively, compounds 3–9 of Table 1 below.

EXAMPLE 2

Step A: Ethyl 2-(5-fluoro-2-nitrophenoxy)acetate

A stirred mixture of 30.0 grams (0.19 mole) of 5-fluoro-2-nitrophenol, 35.1 grams (0.21 mole) of ethyl bromoacetate, and 30.0 grams (0.22 mole) of potassium carbonate in 250 ml of acetone was heated at reflux for three hours. The mixture was cooled and poured into water. This mixture was extracted with methylene chloride, and the extract was washed with an aqueous, saturated sodium chloride solution. The washed extract was dried over anhydrous magnesium sulfate and filtered. The filtrate was evaporated under reduced pressure, leaving an oil which solidified upon standing. This solid was triturated with petroleum ether to yield 49.0 grams of ethyl 2-(5-fluoro-2-nitrophenoxy) acetate; another sample of this compound prepared in the same manner, had a melting point of 42°–44° C. and an nmr spectrum which was consistent with the proposed structure.

Step B: 7-Fluoro-2H-1,4-benzoxazin-3(4H)-one

A solution of the 49.0 grams (0.20 mole) of ethyl 2-(5-fluoro-2-nitrophenoxy)acetate in 100 ml of glacial acetic acid was added to a warm (60° C.), stirred mixture of iron powder (50.0 grams, 0.90 mole) in 300 ml of glacial acetic acid. The reaction temperature was allowed to reach 100° C., and the mixture was stirred for approximately three hours. This mixture was poured into water, forming a precipitate. The precipitate was collected by filtration and was recrystallized from ethanol to yield 25.0 grams of 7-fluoro-2H-1,4-benzoxazin-3(4H)-one; another sample of this compound prepared in a similar manner, and then purified further, has a melting point of 205°–206° C. and an nmr spectrum which was consistent with the proposed structure.

Step C:
7-Fluoro-4-propyl-2H-1,4-benzozazin-3(4H)-one

Under a dry argon atmosphere 2.7 grams of a 60% suspension of sodium hydride in oil (0.068 mole of sodium hydride) was waashed with petroleum ether to remove the oil. To the washed sodium hydride was added 50 ml of N,N-dimethylformamide (DMF), and the mixture was stirred. A solution of 7-fluoro-2H-1,4-benzoxazin-3 (4H)-one (10.0 grams, 0.060 mole) in 50 ml of DMF was added. This mixture was warmed to approximately 40° C. for 30 minutes, and then was cooled to room temperature. A solution of 11.2 grams (0.066 mole) of 1-iodopropane in 10 ml of DMF was added, and the mixture was stirred at room temperature for approximately 18 hours. The reaction mixture was poured into dilute hydrochloric acid and extracted with ethyl acetate. The extract was dried over anhydrous magnesium sulfate and filtered. The filtrate was evaporated under reduced pressure to yield 10.0 grams of 7-fluoro-4-propyl-2H-1,4-benzoxazin-3(4H)-one as an oil.

Another sample of 7-fluoro-4-propyl-2H-1,4-benzoxazin (15.0 grams), which was prepared in the same manner and which had an nmr spectrum that was consistent with the proposed structure, was combined with the product of Step C to provide a total of 25.0 grams.

Step D:
7-Fluoro-6-nitro-4-propyl-2H-1,4-benzoxazin-3(4H)-one

A stirred solution of 20.0 grams (0.096 mole) of 7-fluoro-4-propyl-2H-1,4-benzoxazin-3(4H)-one in 100 ml of concentrated sulfuric acid was cooled to −10°C. A mixture of 10 ml of nitric acid (70% nitric acid by weight in water) and 10 ml of concentrated sulfuric acid was added dropwise during a 20 minute period. After complete addition the mixture was stirred at −5° C. for 10 minutes. The reaction mixture was poured into water which was extracted with ethyl acetate. The extract was dried over anhydrous magnesium sulfate and filtered. The filtrate was evaporated under reduced pressure to leave a tacky solid. This solid was triturated witha mixture of diethyl ether, petroleum ether, and ethyl acetate (1:1:1) to yield, after filtration, 7.2 grams of 7-fluoro-6-nitro-4-propyl-2H-1,4-benzoxazin-3(4H)-one.

The nmr spectrum was consistent with the proposed structure.

Step E:
6-Amino-7-fluoro-4-propyl-2H-1,4-benzoxazin-3(4H)-one

Hydrogenation of 4.7 grams (0.018 mole) of 7-fluoro-6-nitro-4-propyl-2H-1,4-benzoxazin-3(acetate and 175 ml of absolute ethanol with a small amount (approximately 0.025 gram) of platinum (IV) oxide produced 4.3 grams of 6-amino-7-fluoro-4-propyl-2H-1,4-benzoxazin-3(4H)-one as a solid, m.p. 78°–80° C.

The nmr and ir spectra were consistent with the proposed structure.

Step F:
7-Fluoro-4-propyl-2H-1,4-benzoxazin-3(4H)-one-6-yl isocyanate

To a stirred solution of 3.9 grams (0.017 mole) of 6-amino-7-fluoro-4-propyl-2H-1,4-benzoxazin-3(4H)-one in 240 ml of toluene was added a solution of 2.06 grams (0.0104 mole) of trichloromethylchloroformate in 10 ml of toluene. This mixture was stirred at room temperature for 1.5 hours and then was heated at reflux for approximately 18 hours. The mixture was cooled, and the solvent was removed by distillation at atmospheric pressure leaving a residue. This residue was subjected to reduced pressure for two hours to yield 4.36 grams of 7-fluoro-4-propyl-2H-1,4-benzoxazin-3(4H)-one-6 yl is isocyanate as a brown solid.

Step G:
1-(7-Fluoro-4-propyl-2H-1,4-benzoxazin-3(4H)-one-6-yl)-1,4-dihydro-5H-tetrazol-5-one Under a dry nitrogen atmosphere, 4.3 grams of 7-fluoro-4-propyl-2H-1,4-benzoxazin-3(4H)-one-6yl isocyanate and 4.3 g (0.037 mole) of azidotrimethylsilane were heated at reflux for approximately 18 hours. The mixture was allowed to cool to room temperature and was diluted with toluene. This mixture was poured into ice-water forming a precipitate. The precipitate was collected by vaccum filtration, and the filter cake was rinsed first with water followed by diethyl ether. The filter cake was dissolved in acetone, and the organic solution was dried over anhydrous magnesium sulfate. This mixture was filtered, and the filtrate was evaporated under reduced pressure to yield 2.2 grams of 1-(7-fluoro-4-propyl-2H-1,4-benzoxazin-3(4H)-one-6-yl)-1,4-dihydro-5H-tetrazol-5 one as a solid m.p. 145°–148° C.

The nmr and ir spectra were consistent with the proposed structure.

Step H:
1-(7-fluoro-4-propyl-2H-1,4-benzoxazin-3(4H)-one-6-yl)-1,4-dihydro-4-(3fluoropropyl)-5H-tetrazol-5 one To a stirred solution of 1.8 gram (0.0061 mole) of 1-(7-fluoro-4-propyl-2H-1,4-benzoxazin-3(4H)-one-6yl)-1,4-dihydo-5H-tetrazol-5-one in 100 ml of DMF was added 0.085 gram (0.061 mole) of potassium carbonate. This mixture was stirred for approximately 45 minutes, and 1.15 gram (0.074 mole) of 3-fluoropropyl methanesulfonate was added. The reaction mixture was stirred at room temperature for two days and then was poured into 400 ml of water. This mixture was extracted first with ethyl acetate followed by methylene chloride, and extracts were combined. The organic extract was dried over anhydrous magnesium sulfate and filtered. The filtrate was evaporated under reduced pressure to leave a residue. This residue was purified by column chromatography on silica gel, eluting with ethyl acetate:n-hexane (1:1), to yield 1.1 gram of 1-(7-fluoro-4-propyl-2H-1,4-enzoxazin-3(4H)-one-6-yl)-1,4dihydo-4-(3fluoropropyl)-5H-tetrazol-5-one as a clear oil.

The nmr and ir spectra were consistent with the proposed structure.

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules (e.g. for paddy rice) in the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–8% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Other wettable power formulations are:

| Component | % by Wt. |
| --- | --- |
| Active ingredient | 40.00 |
| Sodium ligninsulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium ligninsulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkyl-naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component | % by Wt |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 41.42 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acids esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| | % by Wt. |
|---|---|
| Oil Suspension: | |
| Active ingredient | 25.00 |
| polyoxyethylene sorbitol hexaoleate | 5.00 |
| Highly aliphatic hydrocarbon oil | 70.00 |
| Total | 100.00 |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed. Weed control is achieved at low concentrations of the herbicides of this invention; for instance, using compound 2 of the table 1 below one may achieve good weed control with little or no damage to soybeans at dosages, in the greenhouse, of as low as e.g. about 0.12, 0.06, or 0.03 kg/ha or lower. For field use, about <0.015 and where there are losses of herbicide, larger dosages (e.g. four time the dosages mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl)-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1 3-benzothiadiazin-4-(3H)-one-2,2-dioxide (bentazon); triazine herbicides such as 6-chloro-N-ethyl-N-(1- methylethyl)-1,3,5-triazine-2,4-diamine (atrazine), and 2-[4-chloro-6-(ethylamino)-1,3,5-triazin-2-yl]amino -2-methylpropanenitrile (cyanazine); dinitrolaniline herbicides such as 2,6-dinitro-N,N-dipropyl -4-(trifluoromethyl)benzeneamine (trifluralin); and aryl urea herbicides such as N'-(3,4-dichlorophenyl)-N,N-dimethylurea (diuron) and N,N-dimethyl-N'-[3-(trifluoromethyl)-phenyl]urea (fluometuron); and 2-[(2-chlorophenyl)methyl]-4,4-dimethyl-3-isoxazolidone.

It is apparent that various modifications may be made in the formulation and application of the compounds of this invention without departing from the inventive concepts herein as defined in the claims.

TABLE 1

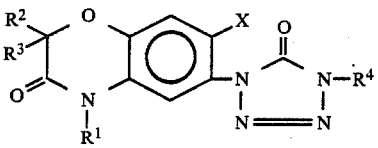

| Cmpd. No. | X | $R^1$ | $R^2$ | $R^3$ | $R^4$ |
|---|---|---|---|---|---|
| 1 | F | H | H | H | $CH_2CH_2CH_2F$ |
| 2 | F | $CH_2CH_2CH_3$ | H | H | $CH_2CH_2CH_2F$ |
| 3 | F | $C_2H_5$ | H | H | $CH_2CH_2CH_2F$ |
| 4 | F | $CH_3$ | H | H | $CH_2CH_2CH_2F$ |
| 5 | F | $CH_2C\equiv CH$ | H | H | $CH_2CH_2CH_2F$ |
| 6 | F | $CH_2OCH_3$ | H | H | $CH_2CH_2CH_2F$ |
| 7 | F | $CH_2SCH_3$ | H | H | $CH_2CH_2CH_2F$ |
| 8 | F | $-CH_2$ phenyl | H | H | $CH_2CH_2CH_2F$ |
| 9 | F | $SO_2C_2H_5$ | H | H | $CH_2CH_2CH_2F$ |
| 10 | F | $SO_2CH_3$ | H | H | $CH_2CH_2CH_2F$ |
| 11 | F | $CH_2CH=CH_2$ | H | H | $CH_2CH_2CH_2F$ |
| 12 | F | $CH_2OC_2H_5$ | H | H | $CH_2CH_2CH_2F$ |
| 13 | Cl | $CH_2C\equiv CH$ | H | H | $CH_2CH_2CH_2F$ |
| 14 | F | $CH_2C\equiv CH$ | H | H | $CH_2CH_2CH_2F$ |
| 15 | F | $CH_2C\equiv CH$ | H | H | $CH_3$ |
| 16 | F | $CH_2C\equiv CH$ | H | H | $C_2H_5$ |
| 17 | F | $CH_2C\equiv CH$ | H | H | $CH_2CH_2CH_3$ |
| 18 | F | $CH_2C\equiv CH$ | H | H | $CH(CH_3)_2$ |
| 19 | F | $CH_2C\equiv CH$ | H | H | $CH_2CH=CH_2$ |
| 20 | F | $CH_2F$ | H | H | $CH_2CH_2CH_2F$ |
| 21 | F | $CH_2CH_2F$ | H | H | $CH_2CH_2CH_2F$ |
| 22 | F | $CH_2CN$ | H | H | $CH_2CH_2CH_2F$ |
| 23 | F | $CH_2CH_2CH_2F$ | H | H | $CH_2CH_2CH_2F$ |
| 24 | F | $CH_2CH_2CN$ | H | H | $CH_2CH_2CH_2F$ |
| 25 | F | $CH_2CH=CH-CH_3$ | H | H | $CH_2CH_2CH_2F$ |
| 26 | F | $CH(CH_3)CH_2CH_3$ | H | H | $CH_2CH_2CH_2F$ |
| 27 | F | $CH_2CH(CH_3)CH_2CH_3$ | H | H | $CH_2CH_2CH_2F$ |
| 28 | F | $OCH_3$ | H | H | $CH_2CH_2CH_2F$ |
| 29 | F | $OCH_2CH_3$ | H | H | $CH_2CH_2CH_2F$ |
| 30 | F | $CH_2SCH_2CH_3$ | H | H | $CH_2CH_2CH_2F$ |
| 31 | F | $CH_2C(CH_3)=CH_2$ | H | H | $CH_2CH_2CH_2F$ |
| 32 | F | $CH_2CH_2CH(CH_3)_2$ | H | H | $CH_2CH_2CH_2F$ |
| 33 | F | $CH_2(CH_2)_3CH_3$ | H | H | $CH_2CH_2CH_2F$ |
| 34 | F | $SO_2CH_2CH_3$ | H | H | $CH_2CH_2CH_2F$ |
| 35 | F | $CH_2C\equiv Cl$ | H | H | $CH_2CH_2CH_2F$ |
| 36 | F | $SO_2CH(CH_3)_2$ | H | H | $CH_2CH_2CH_2F$ |
| 37 | F | $CH_2CH=CH_2$ | H | H | $CH_2CH_2CH_2F$ |

Other representative compounds are identical with compounds 1-37 except that $R^2$ is methyl.

The following tabulation gives herbicidal data for the compound number 2 of Table 1; these data were obtained in the manner described in PCT published application no. WO 85/01939, employing a solution of the compound in 50/50 acetone/water mixture, at a dosage rate of 0.25 of the compound per hectare.

TABLE 2

| | Percent Control | |
|---|---|---|
| Species | Preemergence | Postemergence |
| Cotton | 60 | 95 |
| Soybean | 10 | 80 |
| Field Corn | 95 | 100 |
| Rice | 90 | 80 |
| Wheat | 70 | 70 |
| Morningglory | 60 | 100 |
| Wild Mustard | 100 | 100 |
| Velvetleaf | 100 | 100 |
| Barnyardgrass | 95 | 95 |
| Green Foxtail | 100 | 100 |
| Johnsongrass | 95 | 95 |

We claim:

1. Compound of the formula

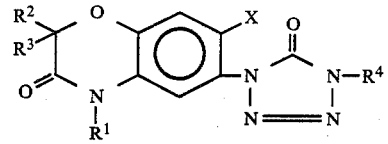

in which $R^1$ is H, alkyl, alkenyl, alkynyl, haloalkyl, haloalkenyl, haloalkynyl, alkoxyalkyl, alkoxyalkoxyalkyl, alkylsulfonyl, aralkyl, alkylthioalkyl, hydroxy or alkoxy;

$R^2$ and $R^3$ are independently H of alkyl;

X is H, Cl or F;

$R^4$ is alkyl, haloalkyl, alkenyl or alkynyl.

2. Compound of claim 1 in which $R^2$ and $R^3$ are H, X is F, $R^4$ is $CH_2CH_2CH_2E$.

3. Compound of claim 2 in which $R^1$ is propynyl.

4. Compound of claim 2 in which $R^1$ is propyl.

5. Compound of claim 2 in which $R^1$ is alkylsulfonyl.

6. An herbicidal composition comprising an herbicidally effective amount of the compound of claim 1 in admixture with a suitable carrier.

7. A method for controlling undesired plant growth which comprises applying to the locus where control is desired an herbicidally effective amount of the composition of claim 6.

8. An herbicidal composition comprising an herbicidally effective amount of the compound of claim 2 in admixture with a suitable carrier.

9. A method for controlling undesired plant growth which comprises applying to the locus where control is desired an herbicidally effective among of the composition of claim 8.

* * * * *

UNITED STATES PATENT AND TRADEMARK OFFICE
CERTIFICATE OF CORRECTION

PATENT NO. : 4,734,124

DATED : March 29, 1988

INVENTOR(S) : Jun H. Chang and John W. Lyga

It is certified that error appears in the above-identified patent and that said Letters Patent is hereby corrected as shown below:

Column 1, line 22, "or methypropynyl" should read --or methylpropynyl--.
Column 2, line 45, "(4H-one" should read --(4H)-one--; line 63, "is the" should read --is then--. Column 3, line 58, "benzozazin" should read --benzoxazin--; line 62, "waashed" should read --washed--. Column 4, line 33, "witha" should read --with a--; line 45, "3 (acetate" should read --3(4H)-one in 50 ml of ethyl acetate--; line 68, "6 yl is isocyanate" should read --6-yl isocyanate--. Column 5, line 6, "6yl" should read --6-yl--; line 19, "5 one" should read --5-one--; line 24, "(3fluoropropyl)" should read --(3-fluoropropyl)--; line 24, "5 one" should read --5-one--; line 28, "6yl)" should read --6-yl)--; line 29, "0.085" should read --0.85--; line 36, "and extracts" should read --and the extracts--; line 42, "4-enzoxazin" should read --4-benzoxazin--; line 42, "4dihydo" should read --4-dihydo--; line 43, "(3fluoropropyl)" should read --(3-fluoropropyl)--. Column 6, line 17, "5-8% should read --5-80%--. Column 7, line 20, "of surfactant" should read --of a surfactant--; line 21, "freqently" should read --frequently--. Column 8, lines 53 and 54, "use about <0.015 and where" should read --use, where--; line 66, "-2,1 3-" should read --2,1, 3 --. Column 10, line 39, "$CH_2CH_2CH_2E$" should read --$CH_2CH_2CH_2F$--.

UNITED STATES PATENT AND TRADEMARK OFFICE
CERTIFICATE OF CORRECTION

PATENT NO. : 4,734,124

DATED : March 29, 1988

INVENTOR(S) : Jun H. Chang and John W. Lyga

It is certified that error appears in the above-identified patent and that said Letters Patent is hereby corrected as shown below:

Column 1, line 21, "or methyallyl" should read --or methylallyl--. Column 4, line 12, "azin (15.0 grams)" should read --azin -3(4H)-one (15.0 grams)--. Column 4, line 60, "trichloromethylchloroformate" should read --trichloromethyl chloroformate--. Column 6, line 25, "power" should read --powder--. Column 7, line 51, "acids" should read --acid--. Column 9, line 3, "dinitrolaniline" should read --dinitroaniline--. Column 10, line 55, "among" should read --amount--.

Signed and Sealed this

Twentieth Day of February, 1990

*Attest:*

JEFFREY M. SAMUELS

*Attesting Officer*   *Acting Commissioner of Patents and Trademarks*